United States Patent [19]

Miller

[11] Patent Number: Plant 6,246

[45] Date of Patent: Aug. 9, 1988

[54] PHILODENDRON PLANT

[75] Inventor: Howard N. Miller, Gainesville, Fla.

[73] Assignee: Cora McColley, Orlando, Fla.

[21] Appl. No.: 874,860

[22] Filed: Jun. 16, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Frank B. Robb

[57] ABSTRACT

A Philodendron plant of very compact rosette form having thick narrowly ovate to elliptic leaves, the leaves being dark-brick red becoming dark-reddish-green when mature. The petioles are black-red, short, thickened and prominently winged.

1 Drawing Sheet

BACKGROUND AND DESCRIPTION OF THE INVENTION

The present invention comprises new and distinct cultivar of Philodendron plant which is the result of selecting a seedling from crosses of the *Philodendrons wendlandii, domesticum, erubescens, imbe,* with an unnamed species, and in turn crossing this selection with *Philodendron cannifolium.* From this cross, a single seedling was selected for propagation which resulted in this invention.

An extensive program of Philodendron hybridization has been carried on in the vicinity of Orlando, Fla. and is being continued. Much of the effort is directed toward developing tough, leathery, Philodendron which are compact, self-heading, excellent keepers and have distinctive color. The Philodendron of the instant invention is very compact, low growing, a true rosette and approaches the above objectives. I have chosen to call it "Prince Albert" for commercial identification.

I have caused this new variety to be asexually reproduced from tip cuttings and from crown off-shoots and determined that it comes true in successive generations. Since the plant is so compact, vegetative propagation is not commercially feasible. The plant can be mass produced by tissue culturing, and has been found to retain its distinctive characteristics through successive asexual reproduction as before stated.

My new variety has been exposed to various conditions in several locations. It has maintained its form and color under adverse conditions, thus is considered to be a superior indoor foliage plant.

The new variety is distinctive from other philodendrons in cultivation and is not described by Graf, Bailey or DAS Pflanzenreich. The variety with which it may be most nearly compared is the Philodendron "Black Cardinal" of U.S. Plant Pat. No. 5,355. This comparison applies only to the dark red color of the two plants. Growth habits of the plants are very dissimilar. There are other differences which are noted hereinafter and make the new variety distinctive.

The new variety is visually distinguished by the following characteristics of the leaf, including a narrowly ovate to elliptic form with cordate base and acute tip. The margin of the leaf is entire.

Pinnate veination is notable, with smooth prominate midribs, being about three fourths of the length.

The petioles are erect, short, thickened and prominently winged with the leaves being nearly horizonal to erect with internodes ½" or less. Since the plant essentially does not have a stem, the petioles appear to be coming from the crown.

The most distinctive aspect of the new variety is its growth habit and the color of the leaves and petioles. To my knowledge this is the most compact philodendron available, and while the leaf shape and size are very different from "Black Cardinal", the general brick-red to black-red color is very similar providing the same spectacular impression. New leaves are brick-red, older leaves black-red and mature leaves are green.

Certain of the physical characteristics of my new variety are of value in the commercial trade including the fact that the plant breaks freely from the crown giving rise to a clump of plants thereby filling the pot, whereas with other philodendrons, three plants are usually planted in a six inch pot to provide a full, well-balanced pot at selling time.

This variety will withstand low light and low soil moisture for weeks. Actually a low soil moisture content is desirable for maintaining a healthy plant in an indoor situation. Low humidity and temperature fluctuations are not particularly troublesome with this plant under most conditions. The leaves are thick and leathery and withstand bruising and dehyration without wilting.

My new variety is moderately resistant to bacterial leaf rot and does not appear to be affected by the physiological problem referred to in the trade as "shot gun" fungus.

Since this plant is very compact, bushy and spreading, the width in a mature plant is most often greater than the height, and does not need staking. An advantage of this plant is that at an early age, four inch pot size, it shows the true color and form of the mature plant. Growth of the younger plants seems to be moderately slow. This comes from the very compact growth habit. Growth rate is average for mature plants. The average height of year-old plants is 12" with 24" diameter. The growth characteristics of this plant make it ideal for dish gardens, drift-wood arrangements, ground cover or fillers in large plantings. It is an excellent low-growing specimen plant.

The growth of the plant indoors is good since it retains its desired form, size and color longer than most Philodendrons known to be currently available.

Since the instant variety shares some of the characteristics of prior Philodendron varieties and specifically those of U.S. Plant Pat. No. 5,355 "Black Cardinal", specific reference thereto is omitted and the details of the instant variety are emphasized in the following detailed specifications, based on observations made in the vicinity of Orlando, Fla.

The accompanying drawing forming a part of this disclosure, shows a typical plant of the new variety with the colors being as nearly true as possible in illustrating the variety hereof made by photographic means.

Color references are made to the Nickerson Color Fan published by Munsell Color Company, with observations being recorded by daylight illumination under vinyl of not more than 30% shade.

FORM CHARACTERISTICS

1. Leaf shape:
   a. *Mature.*—Ovate to elliptic.
   b. *Immature.*—Narrowly ovate.
   c. *Tip.*—Acute.
   d. *Base.*—(1) Mature: Cordate. (2) Immature: Cordate.
   e. *Displacement.*—Undulate.
   f. *Margin.*—Entire.
   g. *Veination.*—Smooth midrib, sunken veins.
2. Leaf attachment: Petiolate.
3. Leaf arrangement: Alternate; slightly horizontal to vertical.
4. Petiole: Short, erect, thickened, distinctly winged at base of plant.
5. Stem: Very short, appears to be nonexistent, leaves arise from thickened crown.
6. Overall appearance: Compact, self-heading, true rosette, free standing.

SIZE CHARACTERISTICS OF TYPICAL COMMERCIAL SIZE

1. Leaf:

a. *Width-widest point.*—6".
   b. *Width-1" from top.*—1"-1¼".
   c. *Length.*—10".
   d. *Thickness.*—0.016".
2. Petioles:
   a. *Length.*—7".
   b. *Diameter (center).*—½".
   c. *Internode spacing.*—¼" to ½".
   d. *Stem diameter.*—1".

COLOR CHARACTERISTICS

1. Leaf (mature):
   a. *Top.*—27-16.
   b. *Bottom.*—28-15.
2. Leaf (immature):
   a. *Top.*—33-16.
   b. *Bottom.*—35-16.
3. Leaf veination:
   a. *Midrib.*—29-16.
   b. *Veins.*—30-16.
4. Stem (darker): 41-16.
5. Petiole (darker): 41-16.

I claim:

1. A new and distinct variety of Philodendron plant, substantially as herein shown and described, characterized particularly as to novelty by the unique combination of compact rosette form with thick narrowly ovate to elliptic leaves, which are dark, brick-red color as new leaves becoming dark-reddish-green at maturity, petioles of black-red, short thickened prominently winged form, presenting over all a very compact, bushy, spreading plant of a height substantially less than its spread.

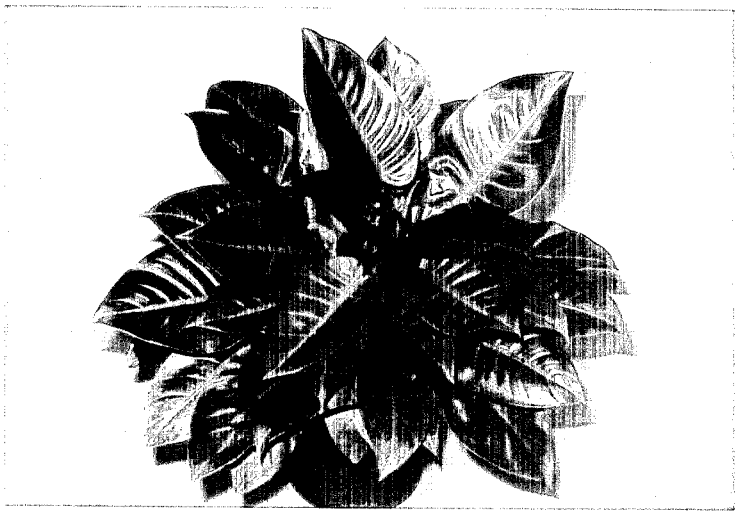

* * * * *